United States Patent [19]

Davison et al.

[11] Patent Number: 5,324,299

[45] Date of Patent: Jun. 28, 1994

[54] ULTRASONIC SCALPEL BLADE AND METHODS OF APPLICATION

[75] Inventors: Thomas W. Davison, North Attleboro; Bernard F. Galat, Newburyport; Stephen Dimatteo, Seekonk, all of Mass.

[73] Assignee: Ultracision, Inc., Smithfield, R.I.

[21] Appl. No.: 829,345

[22] Filed: Feb. 3, 1992

[51] Int. Cl.$^5$ .............................................. A61B 17/32
[52] U.S. Cl. ...................... 606/167; 606/169; 606/170; 604/49
[58] Field of Search ................ 604/22, 49; 606/167, 606/169-171, 39.45, 159, 161, 166, 167; 128/24 AA, 898

[56] References Cited

U.S. PATENT DOCUMENTS

| | | | |
|---|---|---|---|
| 4,188,952 | 2/1980 | Loschilov et al. | 604/22 |
| 4,200,106 | 4/1980 | Douvas et al. | 606/170 |
| 4,428,748 | 1/1984 | Peyman et al. | 606/171 |
| 4,815,462 | 3/1989 | Clark | 604/22 |
| 4,886,491 | 12/1989 | Parisi et al. | 604/22 |
| 4,962,755 | 10/1990 | King et al. | 604/22 |
| 5,013,312 | 5/1991 | Parins et al. | 606/37 |
| 5,026,387 | 6/1991 | Thomas | 606/169 |
| 5,047,043 | 9/1991 | Kubota et al. | 606/169 |
| 5,057,119 | 10/1991 | Clark et al. | 606/169 |
| 5,163,433 | 11/1992 | Kagawa et al. | 604/22 |
| 5,180,363 | 1/1993 | Idemoto et al. | 606/39 |
| 5,188,102 | 2/1993 | Idemoto et al. | 128/24 AA |

FOREIGN PATENT DOCUMENTS 1155256  5/1985  U.S.S.R. ................ 606/169

OTHER PUBLICATIONS

"Valleylab Laparoscopic Instrumentation" brochure, Valleylab, Inc. 1991.

Primary Examiner—C. Fred Rosenbaum
Assistant Examiner—Michael Rafa
Attorney, Agent, or Firm—Nixon & Vanderhye

[57] ABSTRACT

Disclosed is a ultrasonic scalpel blade with a hook and having flat, non-sharpened, relatively dull edges to improve ultrasonic coupling to adjacent tissue and afford exceptional coagulation and hemostasis. The blade with hook is particularly useful for cutting loose, unsupported tissue by grasping the tissue with the hook portion and tensioning it while cutting. The blade affords improved coagulation and hemostasis in loose, unsupported tissue, while simultaneously providing an improved cutting action.

25 Claims, 3 Drawing Sheets

ULTRASONIC SCALPEL BLADE AND METHODS OF APPLICATION

BACKGROUND AND SUMMARY OF INVENTION

The present invention relates to ultrasonically energized scalpel blades and particularly to blades having improved configurations for cutting and coagulating tissue.

In my prior application Ser. No. 07/771,182, filed Oct. 4, 1991, the disclosure of which is incorporated herein by reference, an ultrasonic surgical instrument is disclosed which includes an ultrasonic energy source in a handpiece ultrasonically coupled through an extension to a surgical tool, e.g., a surgical blade, at the tip of the blade extension whereby ultrasonic energy is transmitted from the ultrasonic energy source to the surgical blade and coupled with the tissue to which the blade is applied. That ultrasonic surgical blade achieved exceptional coagulation while cutting by reducing the sharpness and, consequently, increasing the dullness or bluntness of the blade, in comparison with standard sharp surgical blades. Prior to the discovery set forth in that application, it was believed that the same sharp blades used in hand-held surgical scalpels should be applied to ultrasonic surgical scalpels. It was discovered, however, that an otherwise dull blade, when coupled ultrasonically to tissue, enhances the sharpness of the blade when applied to incise and dissect, while simultaneously effecting coagulation. Generally, sharp blades pass through the tissue with less force and less tissue coupling and hence produce less coagulation. Thus, to achieve tissue coagulation and hemostasis, ultrasonic scalpel blades need not be as sharp as standard scalpel blades. In that prior application, the relationship between the type of tissue cut and the sharpness or dullness of the blade is set forth.

It has been found, however, that dull blades do not cut particularly well through relatively loose and unsupported tissues, such as fat unless the tissues are supported against a hard surface (to afford effective cutting with simultaneous coagulation). It has been discovered that an ultrasonic blade having a hook portion and formed sufficiently dull can provide both superior coagulation and effective cutting of loose and unsupported tissue. The hook portion of the ultrasonic blade engages the tissue as the blade is drawn along the tissue and allows the blade to grasp and tension the tissue (hence supporting the tissue) to enhance the cutting action. By stretching or tensioning the tissue, the otherwise dull blade is able to effectively cut as well as coagulate relatively loose and unsupported tissue. Consequently, with an ultrasonic blade having a hook portion, a blade may be selected in accordance with its dullness depending upon the type of surgery with the assurance that simultaneous effective cutting and coagulation can be achieved. For example, where it is necessary to afford greater hemostasis, i.e., where a patient will bleed substantially, as in a gall bladder operation, a very dull ultrasonic blade with a hook is preferable. With such a dull hook blade, effective cutting action is achieved and, when greater power is applied, the coupling with the loose and unsupported tissue provides exceptional hemostasis. Even large blood vessels up to 3 millimeters have been hooked and coagulated while being severed. Fat and parenchymous tissue can be cut by ultrasonically activated dissection blades having hook portions that are approximately 25/1000 inches thick with no blade edge. Connective tissues can be cut by blades with hook portions 25/1000 inches thick and having a 60° blade edge or no edge at all. Generally, the hook portion may be sharpened to angles between 30° and 70°. Such dissection blades provide exceptional hemostasis for good cutting, even in fibrous elastic tissues.

It has also been found according to the present invention that the ultrasonic motion is greatest at the tip of the blade and that the surface area at the tip is proportional to the amount of energy that is coupled to the tissues for coagulation. The large surface area facilitates application of adequate pressure to optimize coupling of the ultrasonic energy with the tissue. Consequently, in accordance with the present invention, blades with flat, non-pointed and non-sharpened tips are provided and have proven highly effective for coagulation of bleeders. Such tips penetrate tissues less during coagulation of bleeders than sharpened tips. Flat tips also provide cavitation fragmentation of tissues to facilitate dissection of loose, low density tissues.

Several specific embodiments of blades employing the principles of the present invention are disclosed. In one such blade principally useful in laparoscopic surgery, e.g., gall bladder surgery, there is provided a blade body having a shank, side faces, a tip opposite the shank and side edges extending from the shank to the tip. At least a side edge of the blade and the tip, are unsharpened and are flat. One of the side edges, however, is provided with a recess which defines with the tip a hook between the one side edge and the tip for grasping and tensioning tissue as the blade is drawn along the tissue. With the flat edge of the blade bearing against tissue, the maximum amount of energy is transferred into the tissue, rendering the blade effective to coagulate bleeders. Simultaneously, the hooked portion of the blade grasps and tensions the loose, unsupported tissue to facilitate the cutting action of the blade through the tissue.

In one specific form of the invention, the blade is in the general shape of a spoon. One side edge of the blade, however, has an arcuate recess. That is, an opposite side edge and tip form a continuous convex curve about the periphery of the blade, while the one side edge defining the hooked portion characterized by a concave curve. All of the edges may be flat and unsharpened. Alternatively, the concave surface may be sharpened with an edge angle, preferably from 30° to 70° depending upon the nature of the surgery. This sharpened hook design enables the blade to dissect even unsupported tissues providing effective coagulation of bleeders and exceptional hemostasis. The generally round shape facilitates application to various tissue contours from a single point of entry and helps prevent puncture during coagulation when substantial pressure is applied to couple the ultrasonic energy with the tissues.

In another form of the present invention, there is provided a hooked dissection blade which is for general purpose use rather than specific use, for example, for laparoscopic surgery. In this form of blade, the blade body is essentially planar, having a recessed portion along one, preferably non-sharpened, side edge to form a hook portion with the tip of the blade. A linearly extending portion of the opposite side edge is sharpened, preferably within a range of 25° to 45°. The tip of the blade is flat and extends linearly between the opposite side edges for maximum energy transfer to the tissue during use. Thus, both the linearly extending flat tip and the single straight cutting edge optimizes the coupling of the ultrasonic energy to the tissue to provide exceptional coagulation and hemostasis while the hook portion tensions unsupported tissue to enhance the cutting action.

In both blades specifically described above, i.e., a spoon-shaped hooked blade for laparoscopic surgery and a hooked dissector blade for general purpose, the blade is carried by a blade coupler which has a stepped horn for amplifying the ultrasonic energy transmitted along the blade coupler to the blade. The blade coupler thus steps from one diameter to a reduced diameter, with consequent amplification of the vibratory axial motion. In the blades hereof, the stepped amplifying horn, however, has a radius which reduces the extent of amplification of the axial vibratory motion to preclude the blade from breaking through fatigue. It will be appreciated that it is important that the stepped horn not lie in the vicinity of a node, i.e., a point of minimal or no axial vibratory motion along the blade coupler. Additionally, in the laparoscopic blade hereof, the node is preferably located in the reduced diameter shank of the blade coupler, whereas in the hooked dissector, the node is located in the larger diameter portion of the coupler. In both cases, of course, the nodes cannot lie in any transition area, i.e., at the stepped horn or at the connection between the blade coupler and either the power element or an extension used for laparoscopic surgery. Also, it will be appreciated that the anti-nodes, i.e., the points along the coupler of maximum energy, are located at the connecting point between the blade coupler and either the power element or extension, as applicable, and the tip of the blade.

In a preferred embodiment according to the present invention, there is provided an ultrasonic scalpel blade for an ultrasonic scalpel comprising a blade coupler having a blade body and a shank extending from the blade body for coupling with a source of ultrasonic energy and transmitting the energy to the blade body, the body having side edges and a tip opposite the shank, one of the side edges having a recess formed therein and defining a hook portion between the one side edge and the tip for tensioning tissue as the blade is displaced along the tissue, thereby facilitating cutting and coagulation of the tissue upon application of ultrasonic energy to the tissue.

In a further preferred embodiment according to the present invention, there is provided an ultrasonic scalpel blade for an ultrasonic scalpel comprising a blade coupler having a blade body and a shank extending from the blade body for coupling with a source of ultrasonic energy and transmitting the energy to the blade body, the body having side faces, side edges and a tip opposite the shank, at least one of the side edges having non-sharpened flat edge surfaces extending linearly between opposite side faces of the blade and in a direction generally normal to the side faces to facilitate coagulation of the tissue upon application of ultrasonic energy to the blade and ultrasonically coupling the blade and tissue as the blade is displaced along the tissue.

In a still further preferred embodiment according to the present invention, there is provided a method of incising and coagulating tissue comprising the steps of providing an ultrasonically actuated scalpel blade having side edges, a tip at an end of the blade and a hook along one of the side edges, and simultaneously cutting and coagulating tissue by (i) applying the ultrasonically energized scalpel blade to the tissue and (ii) tensioning the tissue by engaging the tissue with the blade hook as the blade is drawn along the tissue.

Accordingly, it is a primary object of the present invention to provide novel and improved ultrasonic actuated scalpel blades having improved cutting and coagulating characteristics, particularly for use in soft, relatively loose, unsupported tissue.

These and further objects and advantages of the present invention will become more apparent upon reference to the following specification, appended claims and drawings.

BRIEF DESCRIPTION OF THE DRAWING FIGURES

DETAILED DESCRIPTION OF THE DRAWING FIGURES

Reference will now be made in detail to a present preferred embodiment of the invention, an example of which is illustrated in the accompanying drawings.

Figure 1:
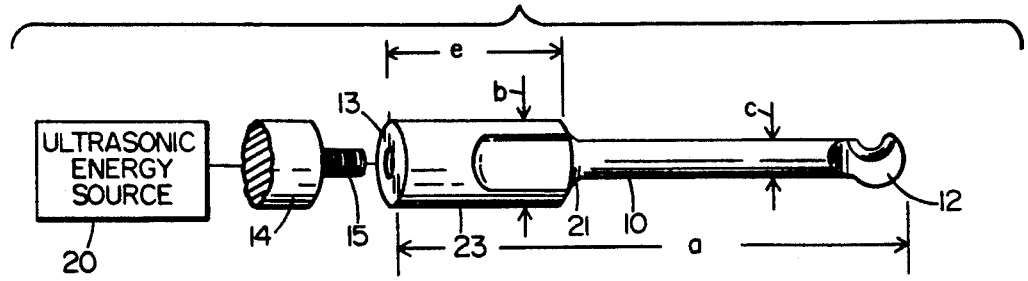
FIG. 1 is a schematic perspective view of a surgical instrument, e.g., a blade coupler with an integral scalpel blade, according to the present invention and illustrated coupled to an extension and an ultrasonic energy source.

Referring now to the drawings, particularly to FIG. 1, there is illustrated a blade coupler 10 having a surgical tool, e.g., an integrally formed scalpel blade 12, at one end and a screw thread for coupling the opposite end of the blade to an acoustical mount. For example, blade coupler 10 is internally threaded at 13 at one end for receiving the external threads of a male connecting portion 15. Because this blade is specifically configured for laparoscopic surgery, the male connecting portion may form part of an extension (described and illustrated in co-pending U.S. patent application Ser. No. 07/828,697, filed Feb. 3, 1992, the disclosure of which is incorporated herein by reference. It will be appreciated that this type of connection is illustrative only and that other types of connections may be formed whereby acoustical energy may be transmitted from the acoustical mount to the blade coupler and to the blade. The acoustical mount, in turn, is coupled to a source of ultrasonic energy within a handle, designated 20, for example, a power element in a handpiece whereby ultrasonic energy is provided blade 12. Generally, the ultrasonic energy source supplies ultrasonic energy at a constant frequency, e.g., 55,500 Hz, to the blade whereby the blade velocity is a function of the electrical power input to the transducer. As indicated above, the blade does not require a mechanical sharpness as in standard disposable scalpel blades in order to have a perceived sharpness corresponding to the sharpness of standard surgical blades. The ultrasonic motion enhances the sharpness. Also, the more dull the blade, the greater will be the transmission of ultrasonic energy to adjoining tissue at the surgical site and an enhanced capacity for hemostasis. As noted previously, however, the efficiency of the cutting action of the dull blade is diminished when the blade is applied for cutting loose, unsupported tissue. In accordance with the present invention, an ultrasonic blade hereof can be sufficiently dull to provide superior coagulation and hemostasis while cutting unsupported tissues by providing the dull blade with a hook portion as will now be described.

Figure 3:
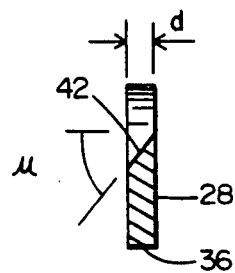
FIG. 3 is a cross-sectional view thereof taken generally about on lines 3—3 in FIG. 2.
Figure 2:
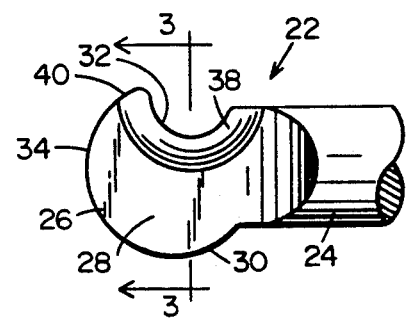
FIG. 2 is a fragmentary side elevational view of the blade illustrated in FIG. 1.

Referring now to a preferred embodiment hereof illustrated in FIGS. 1-3, there is provided a scalpel blade according to the present invention, generally designated 22 and integrally formed at the end of a shank 24 forming part of the blade coupler 10. Blade 22 generally comprises spoon-shaped blade body 26. The blade body has opposite side faces 28, side edges 30 and 32 and a tip 34 opposite the shank 24. As illustrated in FIG. 3, the side edge 30 is flat and unsharpened as at 36 and that flat, unsharpened edge 36 extends along both side edge 30 and tip 34.

The side edge 32 has a recess 38 formed therein which defines a hook portion 40 between the side edge 32 and tip 34. The edge of the recess 38 may be flat and unsharpened similarly as edge 36. Preferably, however, the edge is inclined or sharpened from one side face to the opposite side face. As illustrated in FIG. 3, the recessed edge is sharpened at 42 by inclining the edge from one side face 28 to the opposite side face. The angle of inclination $\mu$ in this form of blade may be approximately 50° as measured from a line perpendicular to the side face 28. Thus, it will be appreciated that the blade has arcuate edges along each of its opposite side edges and tip, with the side edge 30 and tip 34 constituting a flat convex edge surface and the arcuate edge along the one side 32 constituting a concave surface which is preferably sharpened to an angle from one side face of the blade to its opposite side face.

Figure 5:
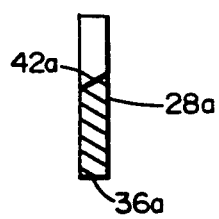
FIG. 5 is a cross-sectional view thereof taken generally about on lines 5—5 in FIG. 4.
Figure 4:
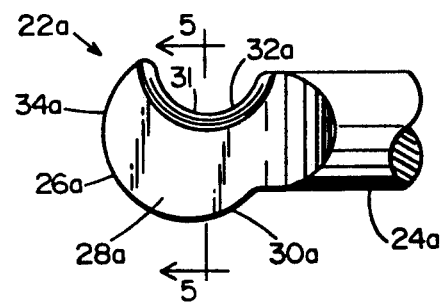
FIG. 4 is a side elevational view of a blade similar to the blade of FIG. 2 and illustrating a different sharpened angle.
Figure 6:
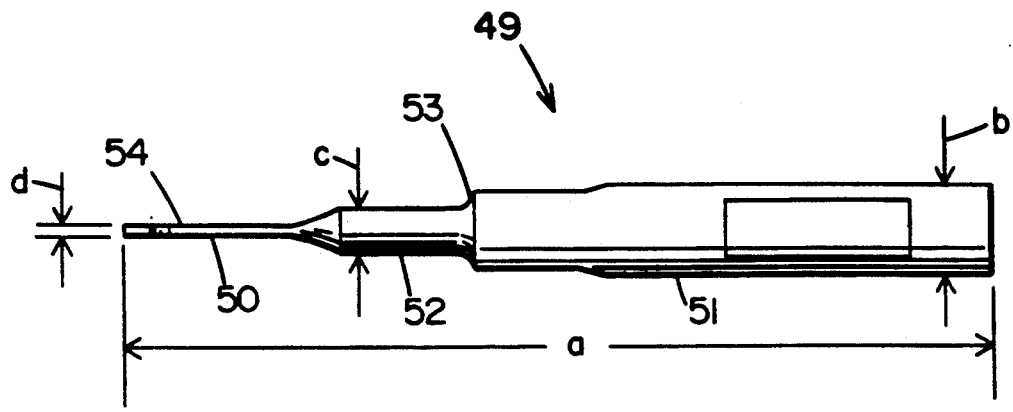
FIG. 6 is a plan view of another embodiment of a blade coupler having a dissector blade.
Figure 7:
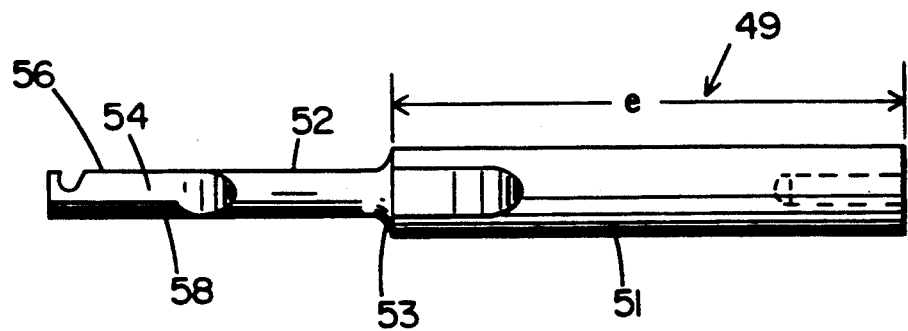
FIG. 7 is a side elevational view thereof.
Figure 10:
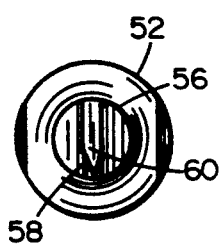
FIG. 10 is an end elevational view thereof.
Figure 8:
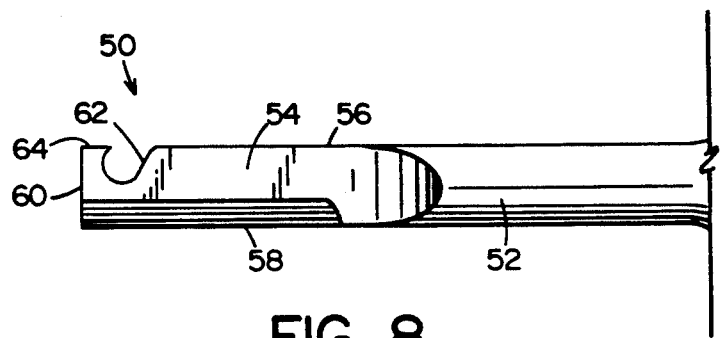
FIG. 8 is an enlarged fragmentary side elevational view of the scalpel blade illustrated in FIGS. 6 and 7.
Figure 9:
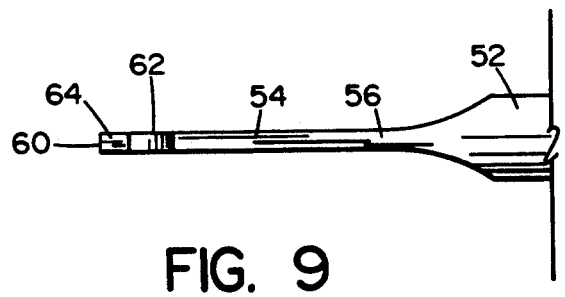
FIG. 9 is a fragmentary top plan view of the blade illustrated in FIGS. 6 and 7.

Referring now to the embodiment hereof illustrated in FIGS. 4 and 5, the blade 22a is substantially identical to the blade 22 of the embodiment hereof illustrated in FIGS. 2 and 3, except that the recessed side edge 32a is sharpened to a different angle. Thus, the edge surface 42a of the side edge 32a is inclined at a lesser angle, for example, on the order of about 30° as measured from a perpendicular to the side face 29a. Preferably, the hook portion is sharpened slightly with a 30° to 70° edge.

The non-sharpened rounded edge at tip 34 or 34a and the non-sharpened edge 30 or 30a of the spoon-shaped blade transfers the maximum amount of energy into the tissues for coagulating bleeders in vascular tissues and coagulating diffuse bleeding from vascular surfaces such as a liver bed. The round shape also facilitates application of the non-sharpened edge to various tissue contours from a single point of entry. The round shape of the spoon blade helps prevent puncture during coagulation of bleeding surfaces when substantial pressure is applied to couple ultrasonic energy with the tissues. This is most important in coagulating the liver bed after dissection of the gall bladder from the liver bed. Dissection is provided by the concave sharpened hook. The hook is preferably sharpened with a 30° to 70° edge. The sharpened hook helps develop tension on the tissues during cutting so that it is very effective in cutting non-supported tissues. In general, less sharp hook blades are used to achieve hemostatic cutting in more vascular or inflamed tissues. Since the hook supports tissues and applies tension as it cuts, a less sharp and more hemostatic edge can be employed for good cutting and most efficient hemostasis.

Referring back to FIG. 1, and referring to both forms of the blade illustrated in FIGS. 2-3 and 4-5, respectively, the blade coupler mounting the integrally formed blade is specifically designed to generate minimum impedance when connected to the end of an extension from the power element in the handpiece of a laparoscopic surgical instrument whereby optimum ultrasonic energy may be transmitted to the blade without undue high power requirements. This is accomplished by designing the blade coupler such that the nodal point lies in the shank portion 24 of the blade, forming the blade of a specific material, i.e., stress-relieved titanium, and providing a stepped horn for amplification of the ultrasonic energy at a location different than the location of the node. Also importantly, the stepped horn is provided with a radius 21 to reduce the amplification of the ultrasonic energy which would otherwise occur by sharply reducing the diameter of the base portion 23 of the coupler to the diameter of the shank portion 24. The radius 21 also prevents the blade 12 from breaking as a result of the applied ultrasonic energy. Note that the stepped horn is located at an axial position other than the node or anti-node points at the opposite ends of the blade coupler.

Certain parameters should be followed in forming the blade 12 and particularly the hooked portion 38 thereof. The hooked portion 38 may not be deeper than the centerline of the coupler, otherwise the ultrasonic energy will cause the blade to fracture and break across the thickness of the blade. Additionally, the hook edge 38 cannot go into the transition area between the round and the flat blade surfaces.

In a preferred embodiment of a blade coupler and blade formed according to the present invention and as illustrated in FIGS. 1-5, the overall blade coupler length "a" is 1.75 inches. The diameter of the base 23 of the coupler at "b" is preferably 0.25 inches, while the diameter of the shank 24 at "c" of the blade coupler 10 is preferably 0.124 inches. The thickness of the blade illustrated at "d" is preferably 0.03 inches and the length "e" of the base 23 of coupler 10 is preferably 0.65 inches. The radius 21 between the base 23 and shank 24 at the stepped horn is 0.06±0.03 inches. Note also the diameter of the spoon-shaped blade without the recess 32 formed therein is the same as the diameter of base 23, i.e., 0.25 inches. The diameter of the spoon portion of the blade, however, may be one-half to two times the diameter of the base 23 of the blade coupler 10.

The ultrasonic blade with hook, as illustrated in FIGS. 1-5, is thus sufficiently dull, e.g., the flat, non-sharpened surfaces 36 along the side edge 30 and the tip 34 to provide superior coagulation when ultrasonically vibrated but, significantly, provides effective cutting in loose, generally unsupported tissues. As the blade is applied along the tissue, the hook portion 40 of the blade grasps the tissue and tensions it to improve the cutting action. At the same time, the flat, unsharpened convex edge of the blade maximizes the transfer of ultrasonic energy to the adjacent tissue for effective coagulation and exceptional hemostasis. The blade is particularly effective for large blood vessels, e.g., up to 3 millimeters, for coagulating the vessels as they are being severed.

Also, it will be appreciated that the ultrasonic motion is greatest at the tip of the blade and that the surface area of the tip is proportional to the amount of energy coupled to the tissues for coagulation. Thus, the ultrasonic coupling of the blade hereof to the tissue affords exceptional coagulation for bleeders because of the non-sharpened flat edge and large surface area contact with the tissue for transferring ultrasonic motion to the tissue.

Referring now to FIGS. 6-10, there is illustrated another form of blade hereof for cutting and dissecting tissue with improved coagulation and hemostasis. This blade is for general purpose use and not for laparoscopic use. The cutting and dissection blade coupler, generally designated 49, comprises a blade 50, a shank 52 and a generally flat blade body 54 having generally linearly extending opposite side edges 56 and 58, terminating in a flat tip 60 extending linearly between the opposite side edges 56 and 58. Coupling of the ultrasonic energy to the tissue is maximized in blades with flat tips and a single straight cutting edge, for example, the relatively sharpened cutting edge 58. The sharpened edge 58 preferably has facets along its opposite sides defining an included angle of about 44°. The non-sharpened linear side edge 56 opposite the sharpened side edge 58 may have one or more recesses forming hooks for use in cutting through loose, unsupported tissue, similarly as in the previous embodiment. The blade with hook therefore includes a recess 62 formed through the side edge 56 forming a hook portion 64 with the tip 60. The edge of the hook portion 62 is flat and non-sharpened similarly as the side edge 56 and tip 60. Alternatively, the edge of the hook portion 62 could be angled as in the previous embodiments within a range of 30° to 70°.

As in the blade coupler of the previous embodiment, the blade coupler 49 is specifically formed to have low impedance to the transmission of ultrasonic energy from the power element in the handpiece to the blade 50. Similarly as in the previous embodiment, the blade is specifically formed to provide a stepped horn for ultrasonic energy amplification at the transition between the base portion 51 and the shank 52 of the blade coupler. Also as in the prior form, the transition between the large diameter base 51 and reduced diameter shank 52 is radiussed at 53. The node, however, in this form is located intermediate the ends of the larger diameter base portion 51. The stepped horn radius is similar to the radius of the previous embodiment, that is, 0.06±0.02 inches. Thus, the stepped horn provides optimal motion at the anti-node, i.e., the tip of the blade. Also, and importantly, by locating the node in the larger diameter base portion 51, more uniform ultrasonic motion along the length of the blade obtains. That is, it is desirable that the motion along the cutting edge 58 be uniform from the tip of the blade to the heel of the sharpened portion 58. While generally the motion is greatest at the tip, by locating the node intermediate the ends of the larger diameter portion 51, the more uniform motion along the length of the cutting edge 50 is provided, e.g., there being no more than about a 20% variation in the motion along the length of the cutting edge 58. Also, the acoustic node cannot be in any transition area, including the stepped horn, or the round to flat blade transition. The flat portion of the blade can be one-half to two times the diameter of the coupler. The hook radius must be 25%±5% of the width of the blade and should be approximately the same distance from the tip of the blade. Otherwise, the blade will break from ultrasonic energy, fatiguing the blade across the width of the blade. In this form of blade, the corresponding dimensions of the blade are as follows: "a" is 2.5 inches; "b" is 0.25 inches; "c" is 0.125 inches; "d" 0.025 inches and "e" is 1.5 inches.

The blades of both embodiments are preferably formed of durable titanium and the blade edges, where sharpened, can be coated with nickel chrome. Titanium has excellent properties for the transfer and amplification of ultrasonic vibrational motion.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

What is claimed is:

1. An ultrasonic scalpel blade comprising:
    a blade coupler having a longitudinally extending blade body defining a plane and a shank extending from said blade body including means for coupling with a source of ultrasonic energy and transmitting the energy to said blade body for vibration thereof longitudinally in said plane;
    said body having side edges and a tip opposite said shank, said side edges and said tip lying in said plane, one of said side edges having means defining a recess and a hook portion along said one side edge spaced from said tip for pulling and tensioning tissue as the blade is displaced along the tissue in a direction parallel to said shank, thereby facilitating cutting and coagulation of the tissue upon application of ultrasonic energy to the tissue, said hook portion being at least in part defined by said recess.

2. A blade according to claim 1 wherein said tip has a flat, non-sharpened end surface.

3. A blade according to claim 1 wherein said blade body has substantially solely arcuate edges along each of its opposite side edges and tip, in said plan the arcuate edges along said tip and the side edge opposite said one side edge being convex and said arcuate edge along said one side edge forming said recess being concave.

4. A blade according to claim 3 wherein said opposite side edges and said tip comprise flat, non-sharpened surfaces and said concave arcuate recessed edge comprises a sharpened edge.

5. A blade according to claim 3 wherein said blade body has opposite side faces, said concave arcuate recessed edge forming an angle as said edge extends from one side face toward the opposite side face.

6. A blade according to claim 1 wherein both of the side edges of said blade body extend laterally beyond the lateral extent of said shank.

7. A blade according to claim 1 wherein the opposite side edges of said blade body extend generally linearly from said shank, with said recess formed through a portion of said one side edge.

8. A blade according to claim 7 wherein the side edge opposite said one side edge includes an elongated sharpened edge.

9. A blade according to claim 8 wherein said opposite side edge is sharpened to form facets along opposite side faces thereof forming an included angle of about at least about 44°.

10. A blade according to claim 8 wherein said tip has a flat, linearly extending, non-sharpened end surface extending between said opposite side edges.

11. A blade according to claim 1 in combination with a handle and an ultrasonic power element carried by said handle, and means for transmitting ultrasonic energy from said power element to said blade.

12. A blade according to claim 1 wherein said body has generally flat side faces extending generally parallel to one another in said plane, said recess having a radius greater than the width of the blade body between said flat side faces thereof.

13. A blade body according to claim 1 wherein said recess along said one side edge is concave and extends generally for about 180° of arc.

14. A blade body according to claim 1 wherein said recess along said one side edge is concave, said hook portion projecting laterally outwardly beyond the confines of said shank.

15. A blade body according to claim 1 wherein said body has generally flat side faces extending generally parallel to one another in said plane, said recess having a radius greater than the width of the blade body between said flat side faces thereof, said recess along said one side edge being concave and extending generally for about 180° of arc, said hook portion projecting laterally outwardly beyond the confines of said shank.

16. An ultrasonic scalpel blade comprising:
 a blade coupler having a blade body and a shank extending from said blade body including means for coupling with a source of ultrasonic energy and transmitting the energy to said blade body;
 said body having side faces, side edges and a tip opposite said shank, at least one of said side edges having non-sharpened flat edge surfaces extending linearly between opposite side faces of said blade and in a direction generally normal to said side faces to facilitate coagulation of the tissue upon application of ultrasonic energy to the blade and ultrasonically coupling the blade and tissue as the blade is displaced along the tissue; and
 said tip having a flat, linearly extending, non-sharpened end surface extending between said opposite side edges.

17. An ultrasonic scalpel blade comprising:
 a blade coupler having a blade body and a shank extending from said blade body including means for coupling with a source of ultrasonic energy and transmitting the energy to said blade body;
 said body having side edges and a tip opposite said shank, one of said side edges having means defining a recess and a hook portion along said one side edge spaced from said tip for pulling and tensioning tissue as the blade is displaced along the tissue, said tip having a blunt surface to facilitate coupling of the blade to the tissue when ultrasonic energy is applied and transmitted to the blade body, whereby coagulation of the tissue upon application of ultrasonic energy to the tissue is facilitated.

18. A blade according to claim 17 wherein said blunt tip is substantially flat in a direction normal to a plane passing through said side edges and said shank.

19. An ultrasonic scalpel blade comprising:
 a blade coupler having a blade body and a shank extending from said blade body including means for coupling with a source of ultrasonic energy and transmitting the energy to said blade body;
 said body having side edges and a tip opposite said shank, one of said side edges having a recess formed therein and defining a hook portion along said one side edge spaced from said tip for pulling and tensioning tissue as the blade is displaced along the tissue in a direction parallel to said shank, thereby facilitating cutting and coagulation of the tissue upon application of ultrasonic energy to the tissue;
 said blade body having arcuate edges along each of its opposite side edges and tip, the arcuate edges along said tip and the side edge opposite said one side edge being convex and said arcuate edge along said one side edge forming said recess being concave; and
 said opposite side edges and said tip comprising flat, non-sharpened surfaces and said concave arcuate recessed edge comprising a sharpened edge.

20. An ultrasonic scalpel blade comprising:
 a blade coupler having a blade body and a shank extending from said blade body including means for coupling with a source of ultrasonic energy and transmitting the energy to said blade body;
 said body having side edges and a tip opposite said shank, one of said side edges having a recess formed therein and defining a hook portion along said one side edge spaced from said tip for pulling and tensioning tissue as the blade is displaced along the tissue in a direction parallel to said shank, thereby facilitating cutting and coagulation of the tissue upon application of ultrasonic energy to the tissue;
 said blade body having arcuate edges along each of its opposite side edges and tip, the arcuate edges along said tip and the side edge opposite said one side edge being convex and said arcuate edge along said one side edge forming said recess being concave; and
 said blade body having opposite side faces, said concave arcuate recessed edge forming an angle as said edge extends from one side face toward the opposite side face.

21. A blade according to claim 20 wherein said angle is about 30°.

22. A blade according to claim 20 wherein said angle is about 50°.

23. A blade according to claim 20 wherein said angle lies within a range of 30°-70°.

24. An ultrasonic scalpel blade comprising:
 a blade coupler having a blade body and a shank extending from said blade body including means for coupling with a source of ultrasonic energy and transmitting the energy to said blade body;
 said body having side edges and a tip opposite said shank, one of said side edges having a recess formed therein and defining a hook portion along said one side edge spaced from said tip for pulling and tensioning tissue as the blade is displaced along the tissue in a direction parallel to said shank, thereby facilitating cutting and coagulation of the tissue upon application of ultrasonic energy to the tissue;
 said opposite side edges of said blade body extending generally linearly from said shank, with said recess formed through a portion of said one side edge;
 said side edge opposite said one side edge including an elongated sharpened edge; and said opposite side edge being sharpened to form facets along opposite side faces thereof forming an included angle of about at least 44°.

25. A method of incising and coagulating tissue comprising the steps of:

providing an ultrasonically actuated scalpel blade having a blade body, side edges therealong, a blunt tip at an end of said blade body, a shank extending from said blade body, and a hook along one of said side edges; and simultaneously cutting and coagulating tissue by (i) applying the ultrasonically energized scalpel blade to the tissue and (ii) tensioning the tissue by engaging the tissue with said hook as the blade is drawn along the tissue in a direction generally parallel to said blade body and toward said shank.

* * * * *